United States Patent [19]
Bryant et al.

[11] Patent Number: 6,090,843
[45] Date of Patent: Jul. 18, 2000

[54] BENZOTHIOPHENES COMPOUNDS WHICH HAVE USEFUL PHARMACEUTICAL ACTIVITY

[75] Inventors: Henry Uhlman Bryant; Jeffrey Alan Dodge, both of Indianapolis, Ind.

[73] Assignee: Eli Lilly and Company, Indianapolis, Ind.

[21] Appl. No.: 09/128,873

[22] Filed: Aug. 4, 1998

Related U.S. Application Data

[60] Provisional application No. 60/055,472, Aug. 11, 1997.

[51] Int. Cl.[7] .......................... C07D 333/52; A61K 31/38
[52] U.S. Cl. .......................... 514/443; 514/444; 514/445; 514/448; 549/52; 549/57; 549/58
[58] Field of Search ................... 549/52, 57, 58; 514/443, 444, 445, 448

[56] References Cited

U.S. PATENT DOCUMENTS

| | | | |
|---|---|---|---|
| 3,394,125 | 7/1968 | Crenshaw | 260/326.5 |
| 3,413,305 | 11/1968 | Crenshaw | 260/326.5 |
| 4,133,814 | 1/1979 | Jones et al. | 260/326.55 A |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones | 546/237 |
| 5,395,842 | 3/1995 | Labrie | 514/320 |
| 5,470,854 | 11/1995 | von Angerer et al. | 514/233 |
| 5,472,962 | 12/1995 | Koizumi et al. | 514/233.5 |
| 5,484,795 | 1/1996 | Bryant et al. | 514/319 |
| 5,688,796 | 11/1997 | Cullinan et al. | 514/320 |
| 5,760,030 | 6/1998 | Bryant et al. | 514/320 |

FOREIGN PATENT DOCUMENTS

| | | |
|---|---|---|
| 062 503 | 10/1982 | European Pat. Off. . |
| 729 956 A1 | 9/1996 | European Pat. Off. . |
| 747 380 A1 | 12/1996 | European Pat. Off. . |
| WO 89/02893 | 4/1989 | WIPO . |
| WO 95/10513 | 4/1995 | WIPO . |

OTHER PUBLICATIONS

Crenshaw, R.R., et al., Potential Antifertility Agents, *J. Med. Chem.* vol. 14, No. 12, pp. 1185–1190 (1971).
Jones, C.D., et al., Antiestrogens, *J. Med. Chem.* vol. 27, pp. 1057–1066 (1984).
Jones, C.D., et al., Antiestrogens, *J. Med. Chem.* vol. 35, pp. 931–938 (1992).
Kaufmann, et al., "Hypochloesterolemic Activity of . . . " *J. Pharmacol. Exp. Ther.*, vol. 280, No. 1, Jan. 1997, pp. 146–153.

*Primary Examiner*—Zinna Northington Davis
*Attorney, Agent, or Firm*—Gilbert T. Voy; James J. Sales

[57] ABSTRACT

This invention provides novel benzothiophene compounds of the formula I:

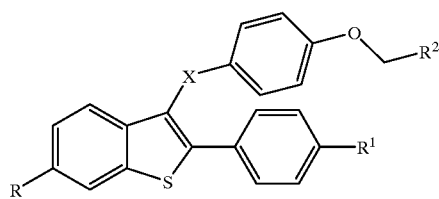

which are useful for the treatment of the various medical conditions associated with postmenopausal syndrome, as well as estrogen dependent diseases including cancer of the breast, uterus, and cervix. The present invention further relates to pharmaceutical formulations of compounds of formula I.

25 Claims, No Drawings

BENZOTHIOPHENES COMPOUNDS WHICH HAVE USEFUL PHARMACEUTICAL ACTIVITY

This Application claims the benefit of U.S. Provisional Application No. 60/055,472, filed Aug. 11, 1997.

FIELD OF INVENTION

This invention relates to the fields of pharmaceutical and organic chemistry and provides novel benzothiophene compounds which are useful for the treatment of the various medical conditions associated with postmenopausal syndrome, as well as estrogen-dependent diseases including cancer of the breast, uterus, and cervix.

BACKGROUND OF THE INVENTION

"Postmenopausal syndrome" is a term used to describe various pathological conditions which frequently affect women who have entered into or completed the physiological metamorphosis known as menopause. Although numerous pathologies are contemplated by the use of this term, three major medical conditions of postmenopausal syndrome are the source of the greatest long-term medical concern: osteoporosis, cardiovascular effects such as hyperlipidemia, and estrogen-dependent cancer such as breast and uterine cancer.

Osteoporosis, which generally includes a group of disorders which arise from diverse etiologies, is characterized by the net loss of bone mass per unit volume.

The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within three to six years after the cessation of menses. This rapid loss is generally associated with an increase of bone resorption and formation. However, the resorptive cycle is more dominant and the result is a net loss of bone mass.

Osteoporosis is a common and serious disease among postmenopausal women. There are an estimated 25 million women in the United States who are afflicted with this disease. The results of osteoporosis disease's sequelae are personally harmful and often result in the need for extensive and long term medical support (hospitalization and nursing home care). This is especially true in elderly patients. Additionally, although osteoporosis is not generally thought of as a life threatening condition, a 20% to 30% mortality rate is related with hip fractures in elderly women. A large percentage of this mortality rate can be directly associated with postmenopausal osteoporosis.

The trabecular tissue is the most vulnerable bone tissue to the effects of postmenopausal osteoporosis. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is loss of the trabeculae which leads to the failure and fracture of bone. In light of the loss of the trabeculae in postmenopausal women, it is not surprising that the most common fractures are those associated with bones which are highly dependent on trabecular support, e.g., the vertebrae and the neck of the weight bearing bones, such as the femur and the fore-arm. Indeed, hip fracture, collies fractures, and vertebral crush fractures are hallmarks of postmenopausal osteoporosis.

At this time, the generally accepted method for treatment of postmenopausal osteoporosis is estrogen replacement therapy (ERT). Although ERT is generally successful, patient compliance with this therapy is low primarily because estrogen treatment frequently produces undesirable side effects.

Prior to menopause, most women have less incidence of cardiovascular disease than age-matched men. Following menopause, however, the rate of cardiovascular disease in women, such as hyperlipidemia, increases to match the rate seen in men. This rapid increase in the incidence of cardiovascular disease has been linked, in part, to the loss of estrogen and to the loss of estrogen's ability to regulate serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, as well as other beneficial effects on cardiovascular health.

It has been reported in the literature that postmenopausal women undergoing estrogen replacement therapy have a return of serum lipid levels to concentrations similar to those of the premenopausal state. Thus, estrogen would appear to be a reasonable treatment for this condition. However, the side-effects of ERT are not acceptable to many women, thus limiting the use of this therapy. An ideal therapy for this condition would be an agent which would regulate the serum lipid levels like estrogen, but would be devoid of the side-effects and risks associated with estrogen therapy.

The third major pathology associated with, but not limited to, postmenopausal syndrome is estrogen-dependent cancer, primarily breast and uterine cancer. Although such neoplasms are not solely limited to postmenopausal women, they are more prevalent in the older postmenopausal population. Current chemotherapy of these cancers has relied heavily on the use of estrogen agonist/antagonist compounds, such as tamoxifen. Although such mixed agonist/antagonists have beneficial effects in the treatment of these cancers, the estrogenic side-effects are tolerable in only acute life-threatening situations. These agents have stimulatory effects on certain cancer cell populations in the uterus due to their estrogenic (agonist) properties and therefore, are contraproductive in some cases. A better therapy for the treatment of these cancers would be an agent which is an antiestrogenic compound in cancerous tissue, having negligible or no estrogen agonist properties on other reproductive tissues.

In response to the clear need for new pharmaceutical agents which are capable of alleviating the symptoms of, inter alia, postmenopausal syndrome, the present invention provides new compounds, pharmaceutical compositions thereof, and methods of using such compounds for the treatment of postmenopausal syndrome and other estrogen-related pathological conditions such as those mentioned herein.

SUMMARY OF THE INVENTION

The present invention relates to compounds of formula I:

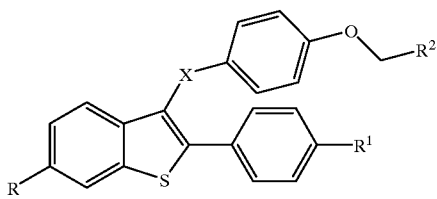

wherein:

R and $R^1$ are independently hydrogen, halo, hydroxy, or O-Pg;

$R^2$ is $CHR^3OR^4$, $CO_2R^5$, $CHOHCH_2NR^6R^7$, or a heterocycle;

X is C=O, CH—OH, $CH_2$, O, or S;

Pg is independently at each occurrence a hydroxy protecting group;

$R^3$ is hydrogen or $CH_2OH$;

$R^4$ is hydrogen, $C_1$–$C_6$ alkyl, or $COR^8$;

$R^5$ is hydrogen, $C_1$–$C_6$ alkyl, or aryl;

$R^6$ and $R^7$ are independently at each occurrence hydrogen or $C_1$–$C_6$ alkyl, or $R^6$ and $R^7$ together with the nitrogen to which they are attached form a 3,5-dimethylpiperidino, 3-methylpiperidino, pyrrolidino, piperidino, or a hexamethyleneimino ring;

$R^8$ is hydrogen, $C_1$–$C_6$ alkyl, or aryl; or a pharmaceutically acceptable salt or solvate thereof.

The present invention further relates to pharmaceutical formulations containing compounds of formula I and the use of such compounds for alleviating the symptoms of postmenopausal syndrome, particularly osteoporosis, cardiovascular-related pathological conditions, and estrogen-dependent cancer.

DETAILED DESCRIPTION OF THE INVENTION

As used herein, the term "$C_1$–$C_4$ alkyl" represents a methyl, ethyl, propyl, isopropyl, cyclopropyl, butyl, cyclobutyl, s-butyl, or a t-butyl group. The term "$C_1$–$C_6$ alkyl" includes "$C_1$–$C_4$ alkyl" groups in addition to straight, branched or cyclic alkyl groups having from five to six carbon atoms which would include, but not be limited to, pentyl, isopentyl, hexyl, 2-methylpentyl, cyclopentyl, cyclohexyl, and like groups. The term "$C_1$–$C_4$ alkoxy" represents a methoxy, ethoxy, propoxy, isopropoxy, butoxy, t-butoxy, or a s-butoxy group. The term "halo" refers to fluoro, chloro, bromo, or iodo.

The term "aryl" represents phenyl, benzyl, substituted phenyl, and substituted benzyl groups.

The term "heterocycle" refers to a 3 or 4 membered saturated, partially unsaturated, or aromatic optionally substituted ring, which contains one heteroatom chosen from oxygen or sulfur, and also refers to a 5 or 6 membered saturated, partially unsaturated, or aromatic optionally substituted ring, which contains one or two heteroatoms chosen from oxygen or sulfur.

The terms "substituted phenyl", "substituted benzyl", and "optionally substituted heterocycle" represent a phenyl, benzyl, or heterocyclic group, respectively, substituted with one to three moieties chosen from the group consisting of halo, hydroxy, nitro, $C_1$–$C_4$ alkyl, $C_1$–$C_4$ alkoxy, trichloromethyl, and trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 2,4-dinitrophenyl, 4-methylphenyl, 4-ethylphenyl, 4-methoxyphenyl, 4-propylphenyl, 4-n-butylphenyl, 4-t-butylphenyl, 3-fluoro-2-methylphenyl, 2,3-difluorophenyl, 2,6-difluorophenyl, 2,6-dimethylphenyl, 2-fluoro-5-methylphenyl, 2,4,6-trifluorophenyl, 2-trifluoromethylphenyl, 2-chloro-5-trifluoromethylphenyl, 3,5-bis-(trifluoromethyl)phenyl, 2-methoxyphenyl, 3-methoxyphenyl, 3,5-dimethoxyphenyl, 2-methyl-4-nitrophenyl, 4-methoxy-2-nitrophenyl, and the like. Examples of a substituted benzyl group would include all the compounds named when the word "benzyl" is substituted for the word "phenyl" in all the previously mentioned examples of a substituted phenyl group. The substitution of a heterocycle is similar to that of phenyl and benzyl group.

The term "hydroxy protecting group" denotes a group understood by one skilled in the organic chemical arts of the type described in Chapter 2 of "Protective Groups in Organic Synthesis, 2nd Edition, T. H. Greene, et al., John Wiley & Sons, New York, 1991, hereafter "Greene".

Representative hydroxy protecting groups include, for example, $C_1$–$C_4$ alkyl and substituted $C_1$–$C_4$ alkyl, including methyl, ethyl, or isopropyl ether, methoxymethyl ether, methylthiomethyl ether, tert-buylthiomethyl ether, (phenyldimethylsilyl)methoxymethyl ether, benzyloxymethyl ether, p-methoxy-benzyloxymethyl ether, and tert-butoxymethyl ether; substituted ethyl ether groups such as ethoxyethyl ether, 1-(2-chloroethoxy)ethyl ether, 2,2,2-trichloroethoxymethyl ether, and 2-(trimethylsilyl)ethyl ether; phenyl and substituted phenyl ether groups such as phenyl ether, p-chlorophenyl ether, p-methoxyphenyl ether, and 2,4-dinitrophenyl ether; benzyl ether groups such as benzyl ether; and alkylsilyl ether groups such as trimethyl-triethyl- and triisopropylsilyl ethers, mixed alkylsilyl ether groups such as dimethylisopropylsilyl ether, and diethylisopropylsilyl ether; ester protecting groups such as those of the general formula $COC_1$–$C_6$ alkyl or COAr, or a formate ester, benzylformate ester, mono- di- and trichloroacetate esters, phenoxyacetate ester, and p-chlorophenoxyacetate and the like; and carbonates of the general formula $COOC_1$–$C_6$ alkyl, or COOAr, where Ar is phenyl or substituted phenyl. The species of hydroxy protecting group employed is not critical so long as the derivatized hydroxy group is stable to the condition of subsequent reaction(s) on other positions of the intermediate molecule and can be selectively removed at the appropriate point without disrupting the remainder of the molecule including any other hydroxy protecting group(s). It is within the knowledge of one skilled in the art to select appropriate hydroxy protecting group(s) for a given set of reaction conditions given the guidance provided by Greene cited above.

The term "carbonyl activating group" refers to a substituent of a carbonyl that promotes nucleophilic addition reactions at that carbonyl. Suitable activating substituents are those which have a net electron withdrawing effect on the carbonyl. Such groups include, but are not limited to, esters and amides such as hydroxybenzotriazole, imidazole, a nitrophenol, pentachlorophenol, N-hydroxysuccinimide, dicyclohexylcarbodiimide, N-hydroxy-N-methoxyamine, and the like; acid anhydrides such as acetic, formic, sulfonic, methanesulfonic, ethanesulfonic, benzenesulfonic, or p-tolylsulfonic acid anhydride, and the like; and acid halides such as the acid chloride, bromide, or iodide.

Although the free-base form of formula I compounds can be used in the methods of the present invention, it is preferred to prepare and use a pharmaceutically acceptable salt form. Typical pharmaceutically acceptable salts include those salts prepared by reaction of the compounds of the present invention with a mineral or organic acid. Such salts are known as acid addition salts. Thus, the term "pharmaceutically acceptable salt" refers to acid addition salts of a compound of formula I which are substantially non-toxic at the doses administered and are commonly used in the pharmaceutical literature. See e.g. Berge, S. M, Bighley, L. D., and Monkhouse, D. C., *J. Pharm. Sci.*, 66, 1, 1977.

Examples of such pharmaceutically acceptable salts are the iodide, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, g-hydroxybutyrate, b-hydroxybutyrate, butyne-1,4-dioate, hexyne-1,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like of a compound of formula I.

By "pharmaceutically acceptable" it is also meant that in a formulation containing the compound of formula I, the carrier, diluent, excipients, and salt must be compatible with the other ingredients of the formulation, and not deleterious to the recipient thereof.

The term "solvate" represents an aggregate that comprises one or more molecules of the solute, such as a formula I compound, with one or more molecules of solvent.

As used herein, the term "effective amount" means an amount of compound of the present invention which is capable of alleviating the symptoms of the various pathological conditions herein described.

The terms "treatment" or "treating" bear their usual meaning which includes prohibiting, inhibiting, ameliorating, halting, restraining, slowing or reversing the progression, or reducing the severity of a pathological symptom related to or resultant from post menopausal syndrome. As such, these methods include both medical therapeutic (acute) and/or prophylactic (prevention) administration as appropriate.

When any of the following substitutions occur:

X is CH—OH; and/or $R^2$ is a heterocycle; and/or $R^2$ is $CHR^3OR^4$ and $R^3$ is $CH_2OH$; and/or $R^2$ is $CHOHCH_2NR^6R^7$;

the compounds of the invention contain chiral centers. All enantiomers, diastereomers, and mixtures thereof, are included within the scope of the present invention. While all diastereomers, both enantiomers, and mixtures thereof, are useful, single enantiomers or single diastereomers are preferred.

While all of the compounds of the present invention are useful, certain of the compounds are particularly interesting and are preferred. The following listing sets out several groups of preferred compounds. It will be understood that each of the listings may be combined with other listings to create additional groups of preferred compounds.

aa) R is halo;

ab) R is fluoro;

ac) R is chloro;

ad) R is bromo;

ae) R is hydrogen;

af) R is hydroxy;

ag) R is O-Pg;

ah) $R^1$ is halo;

ai) $R^1$ is fluoro;

aj) $R^1$ is chloro;

ak) $R^1$ is bromo;

al) $R^1$ is hydrogen;

am) $R^1$ is hydroxy;

an) $R^1$ is O-Pg;

ao) R and $R^1$ are both hydroxy;

ap) R and $R^1$ are both O-Pg;

aq) Pg is methyl;

ar) Pg is benzyl;

as) Pg is isopropyl;

at) $R^2$ is $CHR^3OR^4$;

au) $R^2$ is $CO_2R^5$;

av) $R^2$ is $CHOHCH_2NR^6R^7$;

aw) X is C=O;

ax) X is O;

ay) $R^3$ is hydrogen;

az) $R^3$ is $CH_2OH$;

ba) $R^4$ is hydrogen;

bb) $R^4$ is $C_1$–$C_4$ alkyl;

bc) $R^4$ is t-butyl;

bd) $R^4$ is ethyl;

be) $R^4$ is $COR^8$;

bf) $R^5$ is hydrogen;

bg) $R^5$ is $C_1$–$C_4$ alkyl;

bh) $R^5$ is methyl;

bi) $R^5$ is phenyl;

bj) $R^5$ is benzyl;

bk) $R^6$ hydrogen;

bl) $R^7$ is hydrogen;

bm) $R^7$ is $C_1$–$C_6$ alkyl;

bn) $R^7$ is n-hexyl;

bo) $R^7$ is isopropyl;

bp) $R^7$ is n-butyl;

bq) $R^6$ and $R^7$ together with the nitrogen to which they are attached form a 3,5-dimethylpiperidino ring;

br) $R^6$ and $R^7$ together with the nitrogen to which they are attached form a 3-methylpiperidino ring;

bs) $R^6$ and $R^7$ together with the nitrogen to which they are attached form a pyrrolidino ring;

bt) $R^6$ and $R^7$ together with the nitrogen to which they are attached form a piperidino ring;

bu) $R^8$ is $C_1$–$C_6$ alkyl;
bv) $R^8$ is t-butyl;
bw) $R^8$ is methyl;
bx) $R^8$ is cyclohexyl;
by) $R^8$ is phenyl;
bz) the compound of formula I is a salt;

SYNTHESIS

Specific preparations of compounds of the present invention are described herein, in Examples 1–39. Modification to the methods described below may be necessary to accommodate reactive functionalities of particular substituents. Such modification would be both apparent to, and readily ascertained by, those skilled in the art. The following schemes generally illustrates the preparation of compounds of formula I.

The compounds of formula I where R and $R^1$ are not hydroxy, X is C=O, O, or S, $R^2$ is $CHR^3OR^4$, $CO_2R^5$, or a heterocycle, $R^3$ is hydrogen, and $R^4$ is $C_1$–$C_6$ alkyl may be prepared from compounds of formula II as illustrated in Scheme 1 below where R' and $R^{1'}$ are independently at each occurrence hydrogen, halo, or O-Pg, $R^9$ is $CH_2O(C_1$–$C_6$ alkyl), $CO_2R^5$, or a heterocycle, X' is C=O, O, or S, Y is hydroxy or a leaving group and $R^3$, $R^5$, and heterocycle are as described supra.

Alternatively, when Y is a leaving group in compounds of formula III, IV, or V, displacement of the leaving group by a compound of formula II is accomplished by heating that compound of formula III, IV, or V and a compound of formula II in the presence of an appropriate base, such as potassium bicarbonate or triethylamine, in a polar organic solvent such as N,N-dimethyformamide. The reaction can be conducted at room temperature or, preferably, at 80° C. to 120° C. where the reaction is typically complete in less than 6 hours. The leaving group can be, but is not limited to, halides such as chloride, bromide, or iodide or other functionalities capable of being displaced, such as sulfonates e.g. tosylate and mesylate. The preferred leaving group is bromide.

When $R^9$ in compounds of formula Ia is $CO_2R^5$ and $R^5$ is not hydrogen (esters) such compounds may be converted to their corresponding acids by standard saponifications procedures. This transformation is preferably accomplished through treatment of the ester with aqueous bases such as sodium hydroxide, lithium hydroxide, or potassium hydroxide, followed by acidification with a proton source such as 5N hydrochloric acid.

Compounds of formula I where X is C=O, O, or S, $R^2$ is $CHR^3OR^4$, $R^3$ is hydrogen, and $R^4$ is hydrogen or $COR^8$ may be prepared from compounds of formula Ia where $R^9$ is Scheme 1

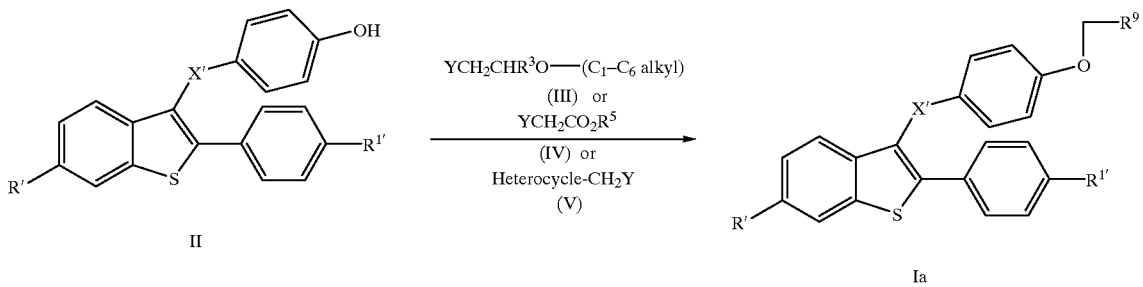

Generally, a phenol intermediate of formula II is reacted with an alkylating agent of formula III, IV, or V under various protocols known in the art to give compounds of formula Ia. In one such procedure, intermediate II is reacted with an alcohol of the formula III, IV, or V under Mitsunobo conditions (Y is hydroxy). The reaction may be accomplished by combining an appropriate alcohol of formula III, IV, or V, a dialkylazodicarboxylate, and a triaryl or trialkylphosphine in a polar organic solvent. Preferred reagents include diethyl azodicarboxylate and triphenylphosphine and the preferred solvents are typically tetrahydrofuran or toluene. Preferred heterocyclic alcohols of formula V are those which contain an oxygen or sulfur atom at least two carbons removed from the alcohol group e.g. 2-hydroxymethyl-2,3,5,6-tetrahydropyrans or 2-thiophenemethanol. The reaction is generally carried out by dissolving the reagents in a suitable solvent between 0° C. and the reflux temperature of the reaction mixture and allowing the reaction to proceed until it is complete, generally in less than 24 hours.

$CH_2O(C_1$–$C_6$ alkyl) as shown in Scheme 2 below where Z is a carbonyl activating group and R, $R^1$, $R^9$, and X' are as described supra.

Scheme 2

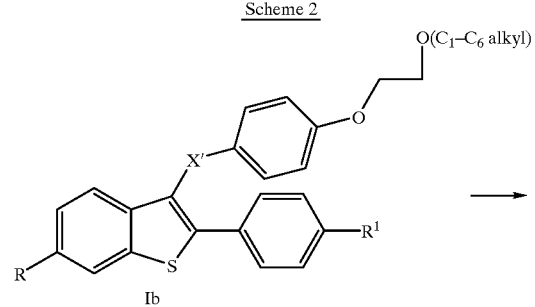

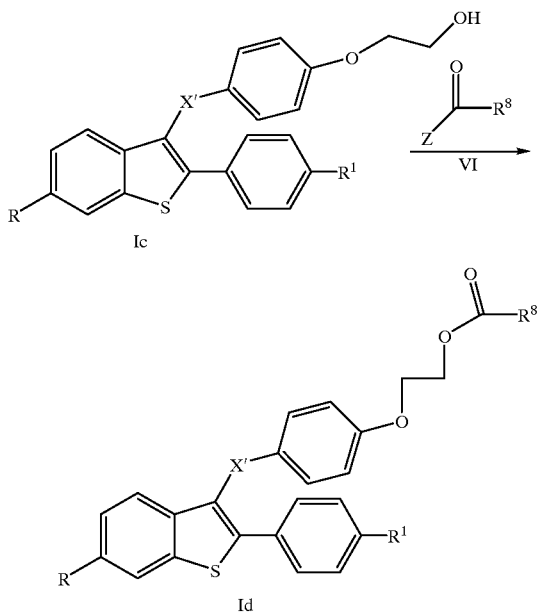

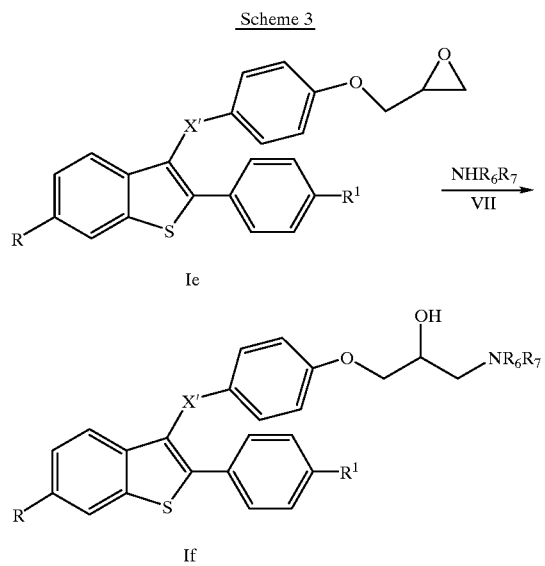

Compounds of formula Ib, prepared as described in Scheme 1, may be converted to compounds of formula Ic using standard hydroxy deprotection conditions known in the art. (See Greene at 14). Compounds of formula Ic may then be esterified using standard conditions well known in the art by treatment with a suitable base and a compound of formula VI. See e.g. Larock, "Comprehensive Organic Transformations", VCH Publishers, Inc., New York, N.Y., 1989, pgs. 978–979. Preferred reagents for this transformation include trialkylamine bases, such as triethylamine, and alkyl or aryl acid chlorides. The reaction is generally carried out in an organic solvent, such as tetrahydrofuran, at room temperature or below and is typically complete in less than 24 hours.

Compounds of formula I where X is C=O, O, or S and $R^2$ is $CHOHCH_2NR^6R^7$ may be prepared from compounds of formula Ia where $R^9$ is a heterocycle where that heterocycle is an epoxide. This transformation is shown in Scheme 3 below where R, $R^1$, $R^6$, $R^7$, and X' are as described supra.

Compounds of formula Ie, prepared as described in Scheme 1, may be reacted with a primary or secondary amine of formula VII e.g. 1-butylamine, pyrrolidine, or piperidine, to provide compounds of formula If. Preferred reaction conditions for this process include reaction of the amine and epoxide in a polar organic solvent, such as methanol or ethanol, at the reflux temperature of the mixture for a period of about 30 minutes to about 4 hours.

The compounds of formula I where X is C=O, O, or S, $R^2$ is $CHR^3OR^4$, $R^3$ is $CH_2OH$, and $R^4$ is hydrogen may be prepared from compounds of formula Ia where $R^9$ is a heterocycle where that heterocycle forms a 1,2-diol protecting group e.g. 2,2-dimethyldioxalan-4-yl. This transformation is illustrated in Scheme 4 below where n is 1 or 2 and R, $R^1$, and X' are as described supra.

Scheme 4

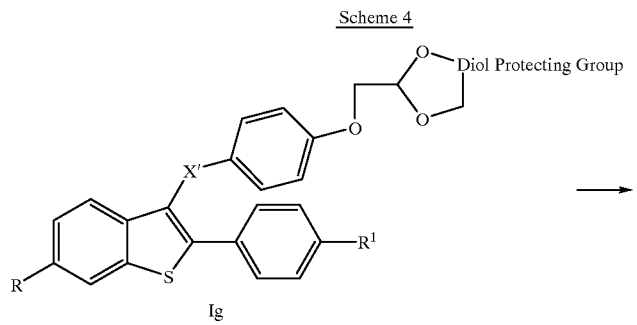

-continued

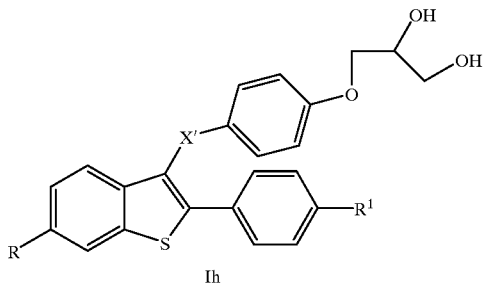

Ih

Compounds of formula Ig, prepared as described in Scheme 1 may be converted to compounds of formula Ic using standard 1,2-dihydroxy deprotection conditions known in the art. See Greene at 118.

The compounds of formula I where X is CH—OH or $CH_2$ may be prepared from compounds of formula Ia-Ih where X is C=O essentially as described in U.S. Pat. No. 5,484,798, the teachings of which are hereby incorporated by reference.

When any of R, R', $R^1$, or $R^{1'}$ are hydroxy protecting groups in compounds of formula Ia-Ih, they may be removed by well known methods in the art to give the compounds of formula I where R and $R^1$ are both hydroxy. Numerous reactions for the formation and removal of hydroxy protecting groups are described in a number of standard works including, for example, *Protective Groups in Organic Chemistry*, Plenum Press (London and New York, 1973); The *Peptides*, Vol. I, Schrooder and Lubke, Academic Press (London and New York, 1965), and Greene. Preferred protecting groups are $C_1$–$C_4$ alkyl groups and especially preferred are methyl groups.

The pharmaceutically acceptable acid addition salts are typically formed by reacting a compound of formula I in its free base form with an equimolar or excess amount of acid. The reactants are generally combined in a polar organic solvent such as methanol or ethyl acetate. The salt normally precipitates out of solution within about one hour to 10 days and can be isolated by filtration, or the solvent can be stripped off by conventional means.

The pharmaceutically-acceptable salts generally have enhanced solubility characteristics compared to the compound from which they are derived, and thus are often more amenable to use in pharmaceutical formulations.

The compounds of formula II may be prepared by a number of well known routes. For example, compounds of formula II where X is C=O and compounds of formula II where X is O, or S can be prepared from m-methoxythiophenol and an appropriately substituted a-bromoacetophenone as taught respectively in U.S. Pat. Nos. 4,133,814 and 5,510,357, the teaching of which are hereby incorporated by reference.

The optimal time for performing the reactions of Schemes 1–4 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. Intermediate and final products may be purified, if desired by common techniques such as recrystallization or chromatography over solid supports such as silica gel or alumina.

Compounds of formula III, IV, V, VI, and VII are either commercially available or may be prepared by methods well known in the art.

The synthetic steps of the routes described herein may be combined in other ways to prepare the formula I compounds. The discussion of the synthesis is not intended to be limiting to the scope of the present invention, and should not be so construed. Application of the above chemistry enables the synthesis of the compounds of formula I, which would include, but not be limited to:

1) [6-hydroxy-2-(4-hydroxyphenyl)benzo[b]thiophen-3-yl][4-(butoxyethoxy)phenyl]methanol,
2) [6-hydroxy-2-(4-hydroxyphenyl)benzo[b]thiophen-3-yl][4-(ethoxyethoxy)phenyl]sulfide,
3) [6-hydroxy-2-(4-hydroxyphenyl)benzo[b]thiophen-3-yl][4-(carboethoxyethoxy)phenyl]ether,
4) [6-hydroxy-2-(4-hydroxyphenyl)benzo[b]thiophen-3-yl][4-([tetrahydrofuran-2-yl]methoxy)phenyl]methane,
5) [6-hydroxy-2-(4-hydroxyphenyl)benzo[b]thiophen-3-yl][4-([tetrahydro-2H-pyran-2-yl]methoxy)phenyl]methanol,
6) [6-hydroxy-2-(4-hydroxyphenyl)benzo[b]thiophen-3-yl][4-(2,3-dihydroxypropoxy)phenyl]sulfide,
7) (R)-[6-hydroxy-2-(4-hydroxyphenyl)benzo[b]thiophen-3-yl][4-(2,3-dihydroxypropoxy)phenyl]ether,
8) [6-hydroxy-2-(4-hydroxyphenyl)benzo[b]thiophen-3-yl][4-(cyclohexanoyloxyethoxy)phenyl]methane
9) [6-hydroxy-2-(4-hydroxyphenyl)benzo[b]thiophen-3-yl][4-([benzoyloxy]ethoxy)phenyl]methanol,
10) [6-hydroxy-2-(4-hydroxyphenyl)benzo[b]thiophen-3-yl][4-([acetoxy]ethoxy)phenyl]sulfide,
11) [6-hydroxy-2-(4-hydroxyphenyl)benzo[b]thiophen-3-yl][4-([trimethylacetoxy]ethoxy)phenyl]ether,
12) [6-hydroxy-2-(4-hydroxyphenyl)benzo[b]thiophen-3-yl][4-(2-hydroxy-3-butylaminopropoxy)phenyl]methane,
13) [6-hydroxy-2-(4-hydroxyphenyl)benzo[b]thiophen-3-yl][4-(2-hydroxy-3-pyrrolidinylpropoxy)phenyl]methanol,
14) [6-hydroxy-2-(4-hydroxyphenyl)benzo[b]thiophen-3-yl][4-(2-hydroxy-3-piperidinylpropoxy)phenyl]sulfide,
15) [6-hydroxy-2-(4-hydroxyphenyl)benzo[b]thiophen-3-yl-[4-(2-hydroxy-3-isopropylaminopropoxy)phenyl] ether,
16) [6-hydroxy-2-(4-hydroxyphenyl)benzo[b]thiophen-3-yl][4-(2-hydroxy-3-[(3a, 5b)-3,5-dimethylpiperidinyl]propoxy)phenyl]methane,
17) [6-hydroxy-2-(4-hydroxyphenyl)benzo[b]thiophen-3-yl][4-(2-hydroxy-3-[(3a, 5a)-3,5-dimethylpiperidinyl]propoxy)phenyl]methanol, 18) [6-hydroxy-2-(4-hydroxyphenyl)benzo[b]thiophen-3-yl][4-(2-hydroxy-3-[3-methylcyclohexyl]propoxy)phenyl]sulfide, and
19) [6-hydroxy-2-(4-hydroxyphenyl)benzo[b]thiophen-3-yl][4-(2-hydroxy-3-pentylaminopropoxy)phenyl]ether.

The following examples further illustrate the processes of the present invention. The examples are not intended to be limiting to the scope of the invention in any respect, and should not be so construed. All experiments were run under positive pressure of dry nitrogen. All solvents and reagents were used as obtained. The percentages are generally calculated on a weight (w/w) basis; except for HPLC solvents which are calculated on a volume (v/v) basis. Proton nuclear magnetic resonance ($^1$H NMR) spectra were obtained on a Bruker AC-300 FTNMR spectrometer operating at 300.135 MHZ.

EXAMPLES

Example 1

[6-Methoxy-2-(4-Methoxyphenyl)benzo[b]thiophen-3-yl][(4-t-Butoxyethoxy)phenyl]methanone

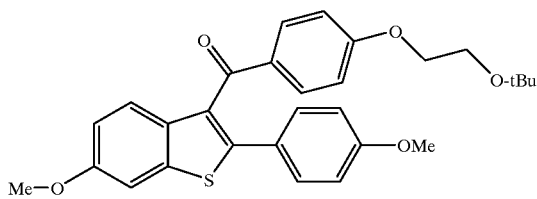

To a mixture of [6-methoxy-2-(4-methoxyphenyl)benzo[b]thiophen-3-yl](4-hydroxyphenyl)methanone (1.0 g, 2.6 mmol), ethylene glycol mono t-butyl ether (0.6 g. 5 mmol), and triphenylphosphine (1.02 g, 3.9 mmol) stirring in tetrahydrofuran (40 mL) at 0° C. was added diethyl azodicarboxylate (0.61 mL, 3.9 mmol) dropwise over a 10 minute period. After 2 hours at room temperature, the reaction was concentrated and the resulting residue purified by flash chromatography (silica gel, 3:1 hexanes/ethyl acetate) to give 1.37 g of the title compound as a thick syrup. Yield: 94%.

Example 2

[6-Methoxy-2-(4-Methoxyphenyl)benzo[b]thiophen-3-yl][(4-Hydroxyethoxy)phenyl]methanone

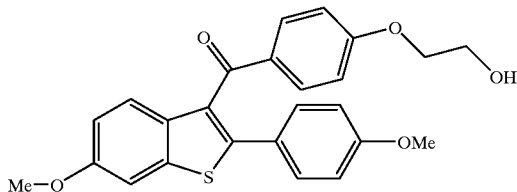

An aqueous solution of sodium hydroxide was added to 1.37 g of [6-methoxy-2-(4-methoxyphenyl)benzo[b]thiophen-3-yl][(4-t-butoxyethoxy)phenyl]methanone stirring in dioxane at room temperature. The mixture was then heated to reflux. After a sufficient time, the mixture was cooled to room temperature and the solution made acidic by addition of 1N hydrochloric acid then extracted with ethyl acetate. The combined organic extracts were washed with brine, dried (sodium sulfate), filtered, and concentrated. This material was purified by flash chromatography (silica gel, ethyl acetate) resulting in 3.0 g of the title compound as a thick syrup.

Example 3

[6-Hydroxy-2-(4-Hydroxyphenyl)benzo[b]thiophen-3-yl][(4-Hydroxyethoxy)phenyl]methanone

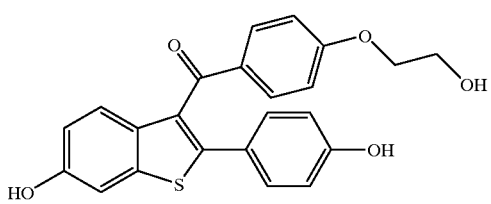

To [6-methoxy-2-(4-methoxyphenyl)benzo[b]thiophen-3-yl][(4-hydroxyethoxy)phenyl]methanone (3.0 g, 6.9 mmol) stirring vigorously in methylene chloride (200 mL) at room temperature was added ethanethiol (3 mL, 40 mmol) followed by aluminum chloride (5.3 g, 40 mmol). After 1 hour, sodium bicarbonate (saturated aqueous solution) and methanol were added. The mixture was then extracted throughout with ethyl acetate. The combined organic extracts were washed with brine, dried (sodium sulfate), filtered, and concentrated. The resulting material was purified by flash chromatography (silica gel, ethyl acetate) to give 2.4 g of the title compound as a yellow solid.

Yield: 85%. $^1$H NMR (C$_3$D$_6$O) d 8.6–8.7 (m,2H), 7.72 (d, J=9.0 Hz, 2H), 7.27 (d, J=8.9 Hz, 2H, 6.84–6.96 (m, 3H), 6.73 (d, J=9.0 Hz, 2H), 4.8 (t, J=3.1 Hz, 2H).

Example 4

[6-Methoxy-2-(4-Methoxyphenyl)benzo[b]thiophen-3-yl][4-(Ethoxyethoxy)phenyl]methanone

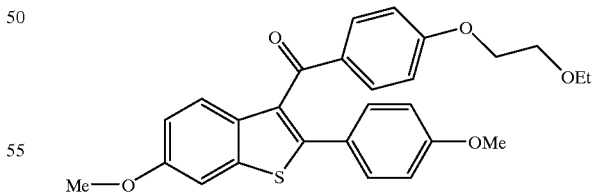

[6-Methoxy-2-(4-methoxyphenyl)benzo[b]thiophen-3-yl](4-hydroxyphenyl)methanone (0.39 g, 1.00 mmol) and ethylene glycol mono ethyl ether (2 mmol) were converted to 350 mg of the title compound by the procedure of Example 1 using 520 mg (2.0 mmol) of triphenylphosphine and 2.0 mmol of diethyl azodicarboxylate the only difference being that the total reaction time was 18 hours.

Example 5

[6-Hydroxy-2-(4-Hydroxyphenyl)benzo[b]thiophen-3-yl][4-(Ethoxyethoxy)phenyl]methanone

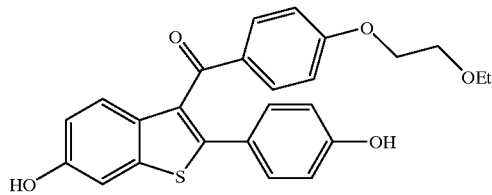

[6-Methoxy-2-(4-methoxyphenyl)benzo[b]thiophen-3-yl][4-(ethoxyethoxy)phenyl]methanone (0.35 g, 0.76 mmol) was converted to 2.4 g of the title compound by the procedure of Example 3 using 0.28 mL (3.79 mmol) of ethanethiol and 0.61 g (4.6 mmol) of aluminum chloride.

Yield: 43%. $^1$H NMR (MeOD): d 7.68–7.71 (d, 2H, J=9.2 Hz), 7.39–7.42 (d, J=8.8 Hz, 1H), 7.25–7.26 (d, 1H, J=2.2 Hz), 7.17–7.19 (d, 2H, J=8.5 Hz), 6.83–6.88 (m, 3H), 6.61–6.64 (d, 2H, J=9.0 Hz), 4.09–4.12 (m, 2H), 3.72–3.75 (m, 2H), 3.52–3.58 (q, 2H, J=7.0 Hz), 1.15–1.20 (t, 3H, J=7.0 Hz).

Example 6

[6-Methoxy-2-(4-Methoxyphenyl)benzo[b]thiophen-3-yl][4-Carbomethoxymethoxyphenyl]methanone

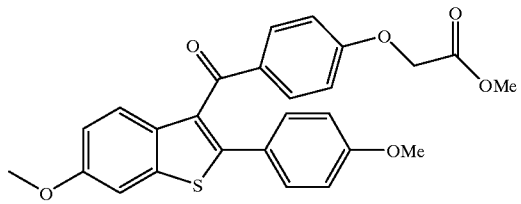

To [6-methoxy-2-(4-methoxyphenyl)benzo[b]thiophen-3-yl](4-hydroxyphenyl)methanone (5.0 g, 12.8 mmol) stirring in dimethylformamide at room temperature was added potassium carbonate (5.3 g, 38.4 mmol) followed by methyl bromoacetate (8 mL, 84.5 mmol). The solution was stirred at 80° C. for 1 hour then cooled to room temperature and poured into brine/ethyl acetate (300 mL, 1:1). The mixture was extracted with ethyl acetate (3×100 mL) and the combined organic extracts washed thoroughly with brine, dried (magnesium sulfate), and filtered. Concentration gave a yellow syrup which was further dried in vacuo to give 5.33 g of the methyl ester as a white crystalline solid which was used without further purification.

Yield: 90%.

Example 7

[6-Hydroxy-2-(4-Hydroxyphenyl)benzo[b]thiophen-3-yl][4-Carbomethoxymethoxyphenyl]methanone

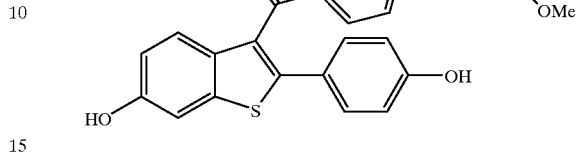

[6-Methoxy-2-(4-methoxyphenyl)benzo[b]thiophen-3-yl][4-carbomethoxymethoxyphenyl]methanone (250 mg, 0.54 mmol) was converted to the title compound by the procedure of Example 3 using 0.24 mL (3.25 mmol) of ethanethiol and 505 mg (3.79 mmol) of aluminum chloride except the total reaction time was 0.5 hours and the workup of the reaction went as follows: the mixture was poured into a mixture of brine/ethyl acetate and extracted with ethyl acetate. The residual solid remaining in the reaction vessel was dissolved in a minimal amount of methanol and added to the ethyl acetate extracts. The combined organic extracts were washed thoroughly with brine, dried (magnesium sulfate), filtered, and concentrated. Purification by radial chromatography (2 mm, silica gel, 40% methanol in ethyl acetate) gave 140 mg methyl ether cleaved product as a yellow solid.

Example 8

[6-Hydroxy-2-(4-Hydroxyphenyl)benzo[b]thiophen-3-yl][4-Carboxymethoxyphenyl]methanone

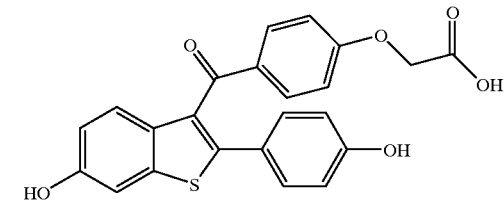

To [6-hydroxy-2-(4-hydroxyphenyl)benzo[b]thiophen-3-yl][4-carbomethoxymethoxyphenyl]methanone (132 mg, 0.30 mmol) stirring in methanol (5 mL) was added sodium hydroxide (0.43 mL of a 5 N aqueous solution, 2.13 mmol). The red mixture was heated to reflux for 0.5 hour, cooled to room temperature, and made acidic with hydrochloric acid (0.70 mL of a 5N aqueous solution). The mixture was then poured into brine and extracted with ethyl acetate. The combined organic extracts were washed thoroughly with brine, dried (magnesium sulfate), and filtered. Concentration afforded the title compound as a yellow solid.

$^1$H NMR($C_3D_6O$): d 8.70 (br s, 2H) 7.76 (d, 2H, J=8.8 Hz), 7.39 (m, 2H), 7.28 (d, 2H, J=9.0 Hz), 6.84–6.94 (d, 2H, J=9.0 Hz), 4.74 (s, 2H)

Example 9

[6-Methoxy-2-(4-Methoxyphenyl)benzo[b]thiophen-3-yl][4-(Tetrahydropyran-2-yl)methoxyphenyl]methanone

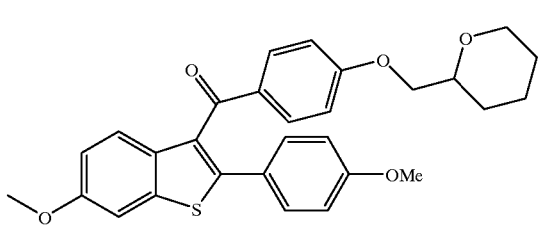

[6-Methoxy-2-(4-methoxyphenyl)benzo[b]thiophen-3-yl](4-hydroxyphenyl)methanone (0.39 g, 1.00 mmol) and 2-hydroxymethyltetrahydropyran (174 mg, 1.5 mmol) were converted to the title compound by the procedure of Example 1 using 390 mg (1.5 mmol) of triphenylphosphine and 0.24 mL (1.5 mmol) of diethyl azodicarboxylate the only difference being that the total reaction time was 3 hours giving a thick syrup.

Example 10

[6-Hydroxy-2-(4-Hydroxyphenyl)benzo[b]thiophen-3-yl][4-(Tetrahydropyran-2-yl)methoxyphenyl]methanone

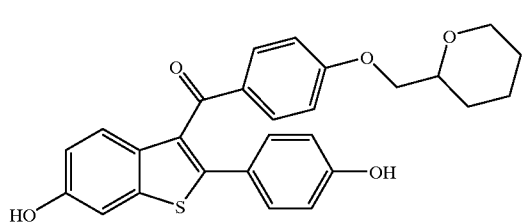

[6-Methoxy-2-(4-methoxyphenyl)benzo[b]thiophen-3-yl][4-(tetrahydropyran-2-yl)methoxyphenyl]methanone (0.32 g, 0.66 mmol) was converted to the title compound by the procedure of Example 3 using 0.24 mL (3.31 mmol) of ethanethiol and 530 mg (3.97 mmol) of aluminum chloride.

Yield: 62%. $^1$H NMR($d_6$-DMSO): d 9.76 (br s, 2H), 7.65 (d, 2H, J=9.0 Hz), 7.35 (d, J=2.0 Hz, 1H), 7.27 (d, J=9.0 Hz, 1H), 7.19 (d, 2H, J=9.0 Hz), 6.85–6.92 (complex, 3H), 6.85 (d, J=9.0 Hz, 2H) 3.85–3.95 (complex, 3H), 3.60 (m, 1H), 1.20–1.82 (complex, 6H).

Example 11

[6-Methoxy-2-(4-Methoxyphenyl)benzo[b]thiophen-3-yl][4-([Tetrahydrofuran-2-yl]methoxy)phenyl]methanone

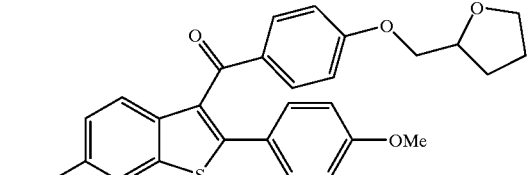

[6-Methoxy-2-(4-methoxyphenyl)benzo[b]thiophen-3-yl](4-hydroxyphenyl)methanone (390 mg, 1 mmol) and 2-hydroxymethyl tetrahydrofuran (153 mg, 1.50 mmol) were converted to 297 mg of the title compound by the procedure of Example 9 using 393 mg (31.5 mmol) of triphenylphosphine and 0.24 mL (1.5 mmol) of diethyl azodicarboxylate the only differences being that the chromatography eluent was 3:7 ethyl acetate:hexanes.

Yield: 83%.

Example 12

[6-Hydroxy-2-(4-Hydroxyphenyl)benzo[b]thiophen-3-yl][4-([Tetrahydrofuran-2-yl]methoxy)phenyl]methanone

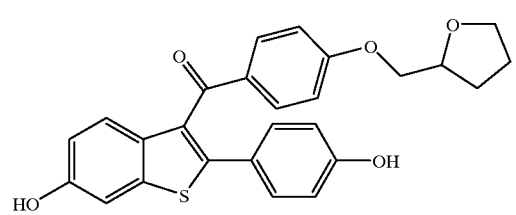

[6-Methoxy-2-(4-methoxyphenyl)benzo[b]thiophen-3-yl][4-([tetrahydrofuran-2-y])methoxy)phenyl]methanone (297 mg) was converted to 189 mg of the title compound by the procedure of Example 3 using 0.24 mL (3.31 mmol) of ethanethiol and 530 mg (3.97 mmol) of aluminum chloride except that 1:1 ethyl acetate:hexanes was used as chromatography eluent.

$^1$H NMR($d_6$-DMSO): d 9.74 (br s, 2H), 7.65 (d, 2H, J=9.1 Hz), 7.35 (d, J=2.5 Hz, 1H), 7.25 (d, 1H, J=9.0 Hz), 7.15 (d, 2H, J=9.3 Hz), 6.93 (d, 1H, J=8.9 Hz), 6.83 (dd, 1H, J=9.0 Hz, 2.3 Hz), 6.70 (d, 2H, J=8.9 Hz), 4.13 (m, 1H), 3.96 (m, 2H), 3.38 (complex, 2H), 1.75–2.0 (complex, 3H), 1.60 (m, 1H).

Example 13

[6-Methoxy-2-(4-Methoxyphenyl)benzo[b]thiophen-3-yl][4-([2,2-Dimethyl-1,3-dioxolan-3-yl]methoxy)phenyl]methanone

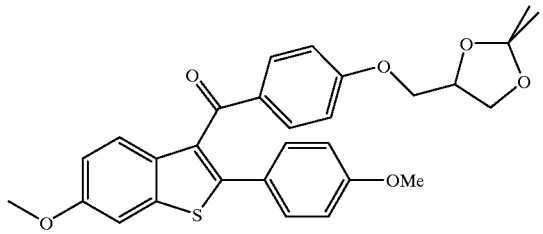

[6-Methoxy-2-(4-methoxyphenyl)benzo[b]thiophen-3-yl](4-hydroxyphenyl)methanone and 2,2-dimethyl-1,3-dioxolane-4-methanol were converted to the title compound by the procedure of Example 9 using triphenylphosphine and diethyl azodicarboxylate.

Example 14

[6-Hydroxy-2-(4-Hydroxyphenyl)benzo[b]thiophen-3-yl][4-(2,3-Dihydroxypropoxy)phenyl]methanone

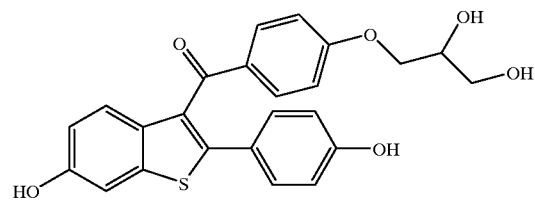

[6-Methoxy-2-(4-methoxyphenyl)benzo[b]thiophen-3-yl][4-([2,2-dimethyl-1,3-dioxolan-3-yl]methoxy)phenyl]methanone was converted to the title compound by the procedure of Example 3 using ethanethiol and aluminum chloride.

Example 15

(R)-[6-Methoxy-2-(4-Methoxyphenyl)benzo[b]thiophen-3-yl][4-([2,2-Dimethyl-1,3-dioxolan-3-yl]methoxy)phenyl]methanone

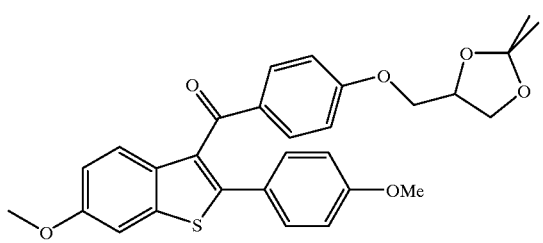

[6-Methoxy-2-(4-methoxyphenyl)benzo[b]thiophen-3-yl](4-hydroxyphenyl)methanone (0.39 g, 1.00 mmol) and (R)-2,2-dimethyl-1,3-dioxolane-4-methanol (0.18 ml, 1.5 mmol) were converted to the title compound by the procedure of Example 13 using 390 mg (1.5 mmol) of triphenylphosphine and 0.24 mL (1.5 mmol) of diethyl azodicarboxylate.

Example 16

(R)-[6-Hydroxy-2-(4-Hydroxyphenyl)benzo[b]thiophen-3-yl][4-(2,3-Dihydroxypropoxy)phenyl]methanone

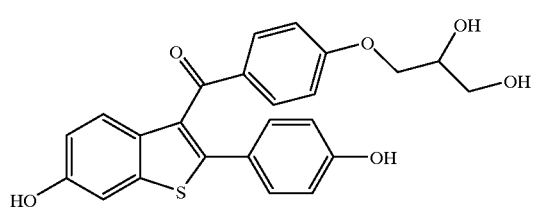

(R)-[6-Methoxy-2-(4-methoxyphenyl)benzo[b]thiophen-3-yl][4-([2,2-dimethyl-1,3-dioxolan-3-yl]methoxy)phenyl]methanone (0.39 g, 0.77 mmol) was converted to the title compound by the procedure of Example 14 using 0.28 mL (3.84 mmol) of ethanethiol and 610 mg (4.61 mmol) of aluminum chloride.

Yield: 82%. $^1$H NMR($d_6$-DMSO): d 9.75 (br s, 2H), 7.68 (d, 2H, J=9.0 Hz), 7.15–7.35 (complex, 4H), 6.82–6.92 (complex, 3H), 6.70 (d, J=9.1 Hz, 2H) 4.98 (d, J=3.1 Hz, 1H), 3.78 (m, 1H), 3.40 (m, 2H).

Example 17

[6-Methoxy-2-(4-Methoxyphenyl)benzo[b]thiophen-3-yl][4-(Cyclohexanoyloxyethoxy)phenyl]methanone

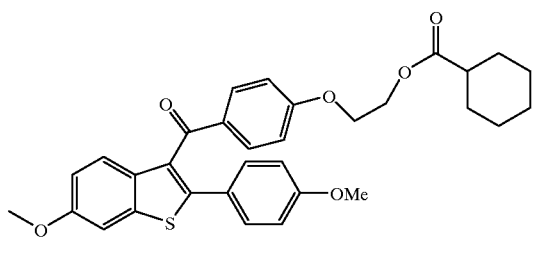

To [6-methoxy-2-(4-methoxyphenyl)benzo[b]thiophen-3-yl][(4-hydroxyethoxy)phenyl]methanone (0.77 g, 1.8 mmol) stirring in tetrahydrofuran (200 mL) was added triethylamine (0.36 g, 3.6 mmol) followed by cyclohexane carbonyl chloride (0.26 g, 1.8 mmol). After 18 hours, the mixture was filtered and concentrated. The resulting material was taken up in ethyl acetate, washed with 1N hydrochloric acid, dried (sodium sulfate), filtered, and concentrated to give 1.25 g of the title compound as a thick oil.

Example 18

[6-Hydroxy-2-(4-Hydroxyphenyl)benzo[b]thiophen-3-yl][4-(Cyclohexanoyloxyethoxy)phenyl]methanone

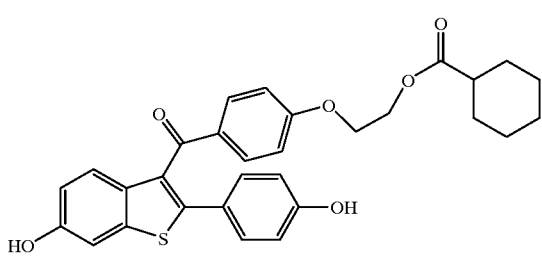

[6-Methoxy-2-(4-methoxyphenyl)benzo[b]thiophen-3-yl][4-(cyclohexanoyloxyethoxy)phenyl]methanone (1.25 g, 2.3 mmol) was converted to the title compound by the procedure of Example 3 using 400 mg (7.0 mmol) of ethanethiol and 920 mg (7.00 mmol) of aluminum chloride (0.92 g, 7.00 mmol).

Yield: 48%. $^1$H NMR($d_6$-DMSO): d 9.75 (app d, 2H), 7.63 (d, 2H, J=8.5 Hz), 7.23 (s, 1H), 7.20–7.23 (m, 1H), 7.13–7.16 (m, 2H), 6.89–6.92 (m, 2H), 6.81–6.83 (m, 1H), 6.64–6.66 (m, 2H), 4.27–4.29 (s, 2H), 4.18–4.20 (s, 2H), 1.62–1.80 (m, 2H), 1.40–1.62 (m, 3H), 1.01–1.39 (m, 6H).

Example 19

[6-Methoxy-2-(4-Methoxyphenyl)benzo[b]thiophen-3-yl][4-(Benzoyloxyethoxy)phenyl]methanone

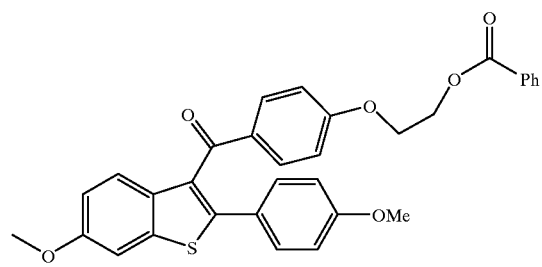

[6-Methoxy-2-(4-methoxyphenyl)benzo[b]thiophen-3-yl][(4-hydroxyethoxy)phenyl]methanone (0.76 g, 1.8 mmol) and benzoyl chloride (0.25 g, 1.8 mmol) were converted to 1.14 g of the title compound by the procedure of Example 17 using 360 mg (3.6 mmol) of triethylamine.

Example 20

[6-Hydroxy-2-(4-Hydroxyphenyl)benzo[b]thiophen-3-yl][4-(Benzoyloxyethoxy)phenyl]methanone

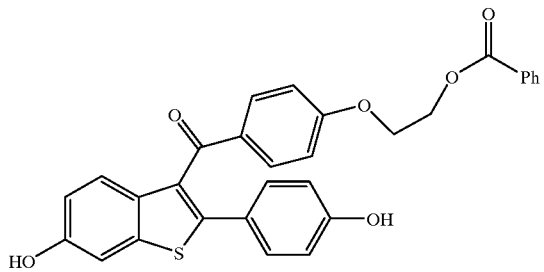

[6-Methoxy-2-(4-methoxyphenyl)benzo[b]thiophen-3-yl][4-(benzoyloxyethoxy)phenyl]methanone (1.14 g, 2.10 mmol) was converted to the title compound by the procedure of Example 3 using 400 mg (7.0 mmol) of ethanethiol and 920 mg (7.0 mmol) of aluminum chloride.

Yield: 20%. $^1$H NMR($d_6$-DMSO): d 9.71–9.76 (d, 2H), 7.90–7.92 (m, 2H), 7.64–7.66 (m, 2H), 7.45–7.47 (m, 2H), 7.31 (s, 1H), 7.14–7.23 (m, 4H), 6.95–6.98 (d, 2H), 6.64–6.67 (d, 2H), 4.56–4.57 (d, 2H), 4.34–4.35 (m, 2H).

Example 21

[6-Methoxy-2-(4-Methoxyphenyl)benzo[b]thiophen-3-yl][4-(Acetoxymethoxy)phenyl]methanone

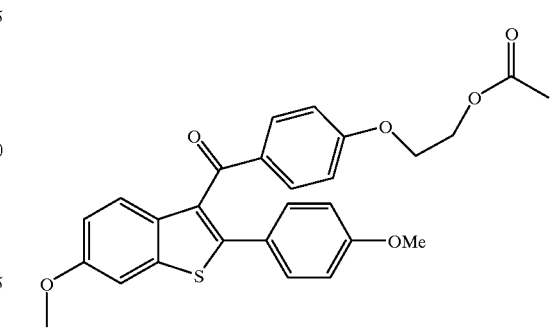

[6-Methoxy-2-(4-methoxyphenyl)benzo[b]thiophen-3-yl][(4-hydroxyethoxy)phenyl]methanone (1.07 g, 2.5 mmol) and acetyl chloride (200 mg, 2.5 mmol) were converted to 1.7 g of the title product by the procedure of Example 17 using 500 mg (5.00 mmol) of triethylamine except that the total reaction time was 72 hours.

Example 22

[6-Hydroxy-2-(4-Hydroxyphenyl)benzo[b]thiophen-3-yl][4-(Acetoxymethoxy)phenyl]methanone

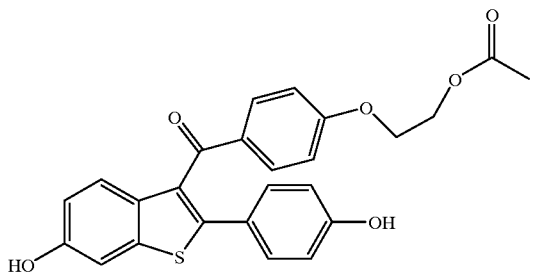

[6-Methoxy-2-(4-methoxyphenyl)benzo[b]thiophen-3-yl][4-(Acetoxymethoxy)phenyl]methanone (1.7 g, 2.5 mmol) was converted to the title compound by the procedure of Example 3 using 500 mg (7.5 mmol) of ethanethiol and 1.0 g (7.5 mmol) of aluminum chloride except that the total reaction time was 4 hours.

Yield: 29%. $^1$H NMR($d_6$-DMSO): d 9.71–9.75 (app d, 2H), 7.63 (d, 2H), 7.32 (s, 1H), 7.23 (d, 1H), 7.15 (d, 2H), 6.90 (d, 2H), 6.83 (d, 1H), 6.64 (d, 2H), 4.28–4.29 (m, 2H), 4.18–4.19 (m, 2H), 1.98 (s, 3H).

Example 23

[6-Methoxy-2-(4-Methoxyphenyl)benzo[b]thiophen-3-yl][4-(Trimethylacetoxymethoxy)phenyl]methanone

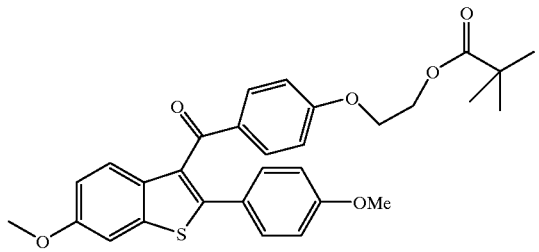

[6-Methoxy-2-(4-methoxyphenyl)benzo[b]thiophen-3-yl][(4-hydroxyethoxy)phenyl]methanone (1.22 g, 2.8 mmol) and trimethyl acetyl chloride (0.34 g, 2.8 mmol) were converted to the title compound by the procedure of Example 21 using 600 mg (5.6 mmol) of triethylamine (0.60 g, 5.6 mmol).

Example 24

[6-Hydroxy-2-(4-Hydroxyphenyl)benzo[b]thiophen-3-yl][4-(Trimethylacetoxymethoxy)phenyl]methanone

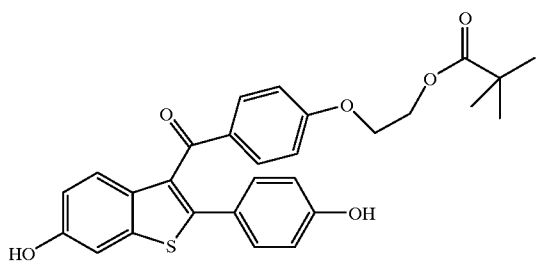

[6-Methoxy-2-(4-Methoxyphenyl)benzo[b]thiophen-3-yl][4-(Trimethylacetoxymethoxy)phenyl]methanone (760 mg, 1.5 mmol) was converted to the title compound by the procedure of Example 3 using 300 mg (4.5 mmol) of ethanethiol and 600 mg (4.5 mmol) of aluminum chloride.

Yield: 69%. $^1$H NMR($d_6$-DMSO): d 9.69 (d, 2H), 7.63 (d, 2H), 7.31 (d, 1H), 7.22 (d, 1H), 7.17 (d, 2H), 6.91 (d, 2H), 6.80 (d, 1H), 6.65 (d, 2H), 4.22–4.28 (m, 2H), 4.20 (m, 2H), 1.04–1.06 (m, 9H).

Example 25

[6-Methoxy-2-(4-Methoxyphenyl)benzo[b]thiophen-3-yl][O-Epihydrin)-4-Hydroxyphenyl]methanone

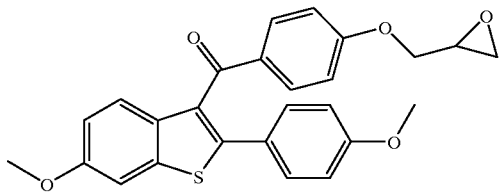

[6-Methoxy-2-(4-methoxyphenyl)benzo[b]thiophen-3-yl](4-hydroxyphenyl)methanone (10 g, 25.6 mmol) and epibromohydrin (3.3 mL, 38.0 mmol) were converted to 2.0 g of the title compound by the procedure of Example 6 except that the reaction was performed for 16 hours at room temperature and the work up was as follows: the reaction mixture was filtered and the filtrate was concentrated. The residue was taken up in ethyl acetate and washed with saturated sodium bicarbonate. The organic portion was dried over sodium sulfate and concentrated to give a yellow solid which was recrystallized from ethyl acetate.

Example 26

[6-Methoxy-2-(4-Methoxyphenyl)benzo[b]thiophen-3-yl][4-(2-Hydroxy-3-Butylaminopropoxy)phenyl] methanone

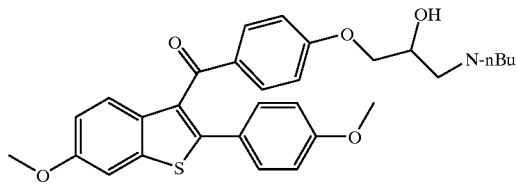

To a suspension of [6-methoxy-2-(4-methoxyphenyl)benzo[b]thiophen-3-yl][O-epihydrin)-4-hydroxyphenyl] methanone (2.0 g, 4.5 mmol) in ethanol (50 mL) was added butylamine (0.98 g, 13.0 mmol) and the reaction mixture was heated to reflux. After 3 hours, the mixture was cooled to room temperature and concentrated. Purification by radial chromatography (silica gel, 4mm, 50% ethyl acetate in hexanes) provided 1.56 g of the title compound as a yellow oil.

Yield: 67%. $^1$H NMR(CDCl$_3$): d 7.76 (d, 2H, J=8.4 Hz), 7.52 (d, 1H, J=9.0 Hz), 7.33 (m, 3H), 6.95 (m, 1H), 6.75 (m, 4H), 3.94 (m, 3H), 3.87 (s, 3H), 3.74 (s, 3H), 2.70 (br m, 6H), 1.39 (br m, 4H), 0.90 (t, 3H, J=7.1 Hz).

Example 27

[6-Methoxy-2-(4-Methoxyphenyl)benzo[b]thiophen-3-yl][4-(2-Hydroxy-3-Pyrrolidinylpropoxy)phenyl] methanone

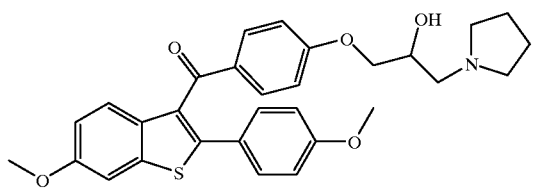

[6-Methoxy-2-(4-methoxyphenyl)benzo[b]thiophen-3-yl][O-epihydrin)-4-hydroxyphenyl]methanone (0.5 g, 1.1 mmol) and pyrrolidine (0.5 mL, 5.0 mmol) were converted to the title compound by the procedure of Example 26 except that 6:4 ethyl acetate/methanol was used as chromatography eluent.

Example 28

[6-Hydroxy-2-(4-Hydroxyphenyl)benzo[b]thiophen-3-yl][4-(2-Hydroxy-3-Pyrrolidinylpropoxy)phenyl methanone

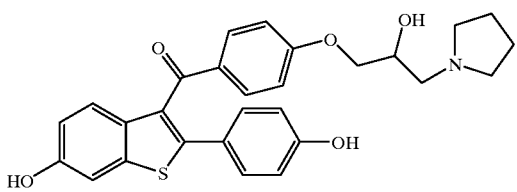

[6-Methoxy-2-(4-methoxyphenyl)benzo[b]thiophen-3-yl][4-(2-hydroxy-3-pyrrolidinylpropoxy)phenyl]methanone (250 mg, 0.50 mmol) was converted to 164 mg of the title compound by the procedure of Example 32 using 0.18 mL (2.48 mmol) of ethanethiol (0.18 mL, 2.48 mmol) and 398 mg (2.98 mmol) of aluminum chloride except that 6:4 ethyl acetate/methanol gradient was used as the chromatography eluent.

$^1$H NMR(d$_6$-DMSO): d 7.62 (d, 2H, J=9.0 Hz), 7.10–7.50 (complex, 4H), 6.80–6.90 (complex, 3H), 6.67 (d, 2H, J=9.0 Hz), 4.12 (m, 1H), 4.00 (m, 1H), 3.81–3.91 (complex, 2H), 2.35–2.60 (complex, 4H), 1.58–1.61 (complex, 4H).

Example 29

[6-Methoxy-2-(4-Methoxyphenyl)benzo[b]thiophen-3-yl][4-(2-Hydroxy-3-Piperidinylpropoxy)phenyl] methanone

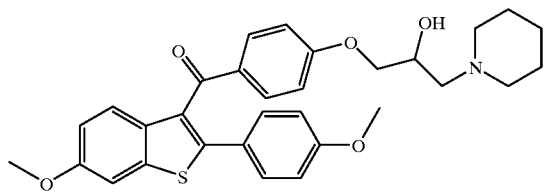

To a solution of [6-methoxy-2-(4-methoxyphenyl)benzo[b]thiophen-3-yl][O-epihydrin)-4-hydroxyphenyl] methanone (0.5 g, 1.1 mmol) stirring in ethanol at room temperature was added potassium carbonate (300 mg, 2.0 mmol) followed by piperidine hydrochloride (200 mg, 1.5 mmol). The mixture was heated to reflux and maintained at that temperature for 1 hour then cooled to ambient temperature. The solution was concentrated and the resulting mixture dissolved in ethyl acetate and extracted with water. The organic extract was dried over magnesium sulfate to give a brown oil which was purified by radial chromatography (silica gel, 2 mm, 8:2 ethyl acetate/methanol (v/v) to give 210 mg of the title compound as an off-white foam.

Example 30

[6-Hydroxy-2-(4-Hydroxyphenyl)benzo[b]thiophen-3-yl][4-(2-Hydroxy-3-Piperidinyl)propoxy]phenyl] methanone

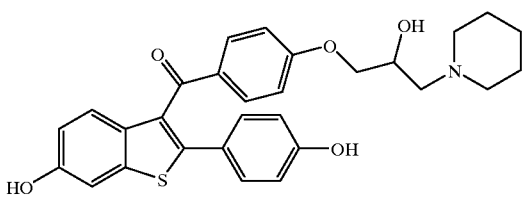

[6-Methoxy-2-(4-methoxyphenyl)benzo[b]thiophen-3-yl][4-(2-hydroxy-3-piperidinylpropoxy)phenyl]methanone (210 mg, 0.41 mmol) was converted to 151 mg of the title compound by the procedure of Example 32 using 0.15 mL (2.03 mmol) of ethanethiol and 326 mg (2.44 mmol) of aluminum chloride.

$^1$H NMR(d$_6$-DMSO): d 7.64 (d, 2H, J=8.8 Hz), 7.34 (d, 1H, J=2.5 Hz 4H), 7.16 (d, 1H, J=9.0 Hz), 6.93 (d, 2H, J=8.7 Hz), 6.84 (dd, J=9.0 Hz, 2.4 Hz), 6.63 (d, 2H, J=8.7 Hz), 3.90–4.10 (complex, 2H), 2.23–2.60 (complex, 6H), 1.45–1.56 (complex, 4H), 1.35–1.45 (complex, 2H).

Example 31

[6-Methoxy-2-(4-Methoxyphenyl)benzo[b]thiophen-3-yl][4-(2-Hydroxy-3-Isopropylamino]propoxy)phenyl]methanone

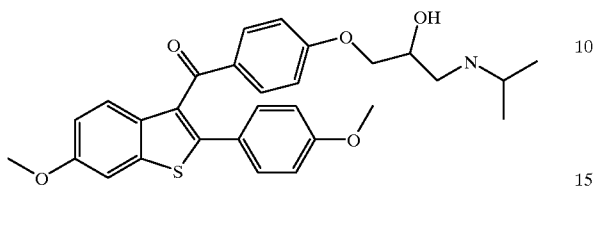

[6-Methoxy-2-(4-methoxyphenyl)benzo[b]thiophen-3-yl][O-epihydrin)-4-hydroxyphenyl]methanone (0.50 g, 1.1 mmol) and isopropylamine (0.48 g, 5.6 mmol) were converted to the title compound by the procedure of Example 26.

Example 32

[6-Hydroxy-2-(4-Hydroxyphenyl)benzo[b]thiophen-3-yl][4-(2-Hydroxy-3-Isopropylamino]propoxy)phenyl]methanone

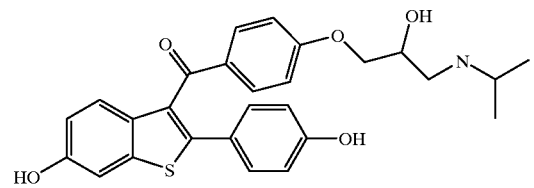

[6-Methoxy-2-(4-methoxyphenyl)benzo[b]thiophen-3-yl][4-(2-hydroxy-3-isopropylamino]propoxy)phenyl]methanone (0.42 g, 0.8 mmol) was converted to 200 mg of the title compound by the procedure of Example 7 using 0.30 mL (4.2 mmol) of ethanethiol and 850 mg (6.4 mmol) of aluminum chloride except that the workup was performed as follows: the reaction was quenched by slow addition of saturated sodium bicarbonate. To the resulting solution was added sufficient methanol to dissolve all remaining yellow residue. This mixture was extracted with ethyl acetate, the combined organic extracts were dried over sodium sulfate, filtered, and concentrated. Purification by radial chromatography (silica gel, 2 mm, 6:2:1.5:0.5 ethyl acetate: hexanes: methanol: triethylamine) provided the desired compound as a yellow solid.

Yield: 52%. $^1$H NMR (CDCl$_3$) d 7.62 (d, 2H, J=8.7 Hz), 7.30 (s, 1H), 7.26 (m, 1H), 7.15 (m, 4H), 6.84 (m, 4H), 6.64 (dd, 2H, J=6.9 Hz, 1.8 Hz), 3.88 (m, 3H), 2.64 (m, 3H), 0.95 (d, 6H, J=6.3 Hz).

Example 33

[6-Methoxy-2-(4-Methoxyphenyl)benzo[b]thiophen-3-yl][4-(3-[2-Hydroxy-(3a, 5b)-3,5-Dimethylpiperidinyl]propoxy)phenyl]methanone, and [6-Methoxy-2-(4-Methoxyphenyl)benzo[b]thiophen-3-yl][4-(2-Hydroxy-3-[(3a, 5a)-3,5-Dimethylpiperidinyl]propoxy)phenyl]methanone

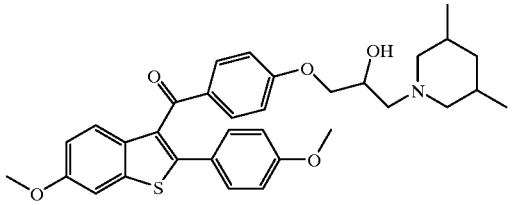

[6-Methoxy-2-(4-methoxyphenyl)benzo[b]thiophen-3-yl][O-epihydrin)-4-hydroxyphenyl]methanone (2.0 g, 4.5 mmol) and 3,5-dimethylpiperidine (2.97, 22.0 mmol) were converted to 670 mg of the trans title product and 1.67 g of the cis title product by the procedure of Example 26. (93% total yield).

Example 34

[6-Hydroxy-2-(4-Hydroxyphenyl)benzo[b]thiophen-3-yl][4-(2-Hydroxy-3-[(3a, 5b)-3,5-Dimethylpiperidinyl]propoxy)phenyl]methanone, and [6-Hydroxy-2-(4-Hydroxyphenyl)benzo[b]thiophen-3-yl][4-(2-Hydroxy-3-[(3a, 5a)-3,5-Dimethylpiperidinyl]propoxy)phenyl]methanone

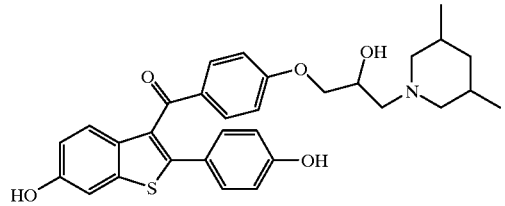

A mixture of [6-hydroxy-2-(4-hydroxyphenyl)benzo[b]thiophen-3-yl][4-(2-hydroxy-3-[(3a, 5b)-3,5-dimethylpiperidinyl]propoxy)phenyl]methanone (670 mg) and [6-methoxy-2-(4-methoxyphenyl)benzo[b]thiophen-3-yl][4-(2-hydroxy-3-[(3a, 5a)-3,5-dimethylpiperidinyl]propoxy)phenyl]methanone (1.67 g) were converted to the title compounds by the procedure of Example 3 to give 500 mg of the trans product and 1.22 g of the cis product.

Yield (trans): 78%. Yield (cis): 78%. $^1$H NMR (CDCl$_3$) trans d 7.61 (d, 2H, J=8.7 Hz), 7.29 (d, 1H, J=2.1 Hz), 7.16 (dd, 3H, J=21 Hz, 8.9 Hz), 6.83 (m, 3H), 6.63 (d, 2H, J=8.4 Hz), 4.79 (br m, 1H), 4.00 (m, 1H), 3.84 (t, 1H, J=6.2 Hz), 3.28 (s, 2H), 3.12 (s, 1H), 2.34(m, 4H), 1.99 (m, 1H), 1.73 (m, 1H), 1.15 (t, 1H, J=5.4 Hz), 0.88 (m, 6H).

$^1$H NMR (CDCl$_3$) cis d 7.61 (d, 2H, J=8.7 Hz), 7.29 (d, 1H, J=2.1 Hz), 7.16 (dd, 3H, J=21 Hz, 8.9 Hz), 6.83 (m, 3H), 6.63 (d, 2H, J=8.4 Hz), 4.78 (br m, 1H), 3.84 (m, 4H), 3.29 (s, 2H), 3.12 (d, 2H, J=2.6 Hz), 2.72 (m, 2H), 2.45 (m, 2H), 2.31 (m, 2H), 1.462 (m, 4H), 0.94 (m, 6H).

Example 35

[6-Methoxy-2-(4-Methoxyphenyl)benzo[b]thiophen-3-yl][4-(2-Hydroxy-3-[3-Methylpiperidinyl] propoxy)phenyl]methanone

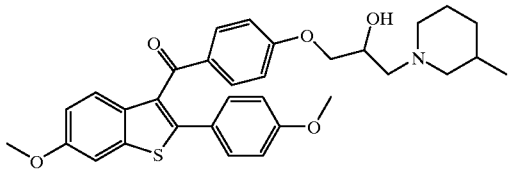

[6-Methoxy-2-(4-methoxyphenyl)benzo[b]thiophen-3-yl][O-epihydrin)-4-hydroxyphenyl]methanone (500 mg, 1.1 mmol) and 3-methylpiperidine (0.65 mL, 5.6 mmol) were converted to 340 mg of the title compound by the procedure of Example 26.

Example 36

[6-Hydroxy-2-(4-Hydroxyphenyl)benzo[b]thiophen-3-yl][4-(2-Hydroxy-3-[3-Methylpiperidinyl] propoxy)phenyl]methanone

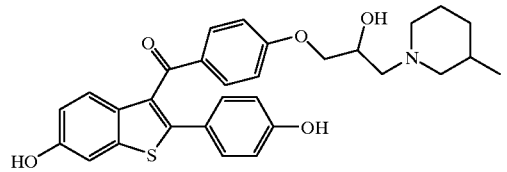

[6-Methoxy-2-(4-methoxyphenyl)benzo[b]thiophen-3-yl][4-(2-hydroxy-3-[3-methylpiperidinyl]propoxy)phenyl]methanone (540 mg, 1.0 mmol) was converted to 340 mg of the title compound by the procedure of Example 32 using 360 mg (4.9 mmol) of ethanethiol and aluminum chloride.

Yield: 66%. $^1$H NMR (CDCl$_3$) d 7.13 (d, 2H, J=8.4 Hz), 6.84 (m, 3H), 6.63 (dd, 2H, J=8.4 Hz), 3.91 (m, 3H), 2.69 (m, 2H), 2.31 (m, 2H), 1.901 (m, 2H), 1.52 (m, 5H), 0.75 (d, 6H, J=5.4 Hz).

Example 37

[6-Methoxy-2-(4-Methoxyphenyl)benzo[b]thiophen-3-yl][4-(2-Methoxy-3-Hexylaminopropoxy)phenyl] methanone

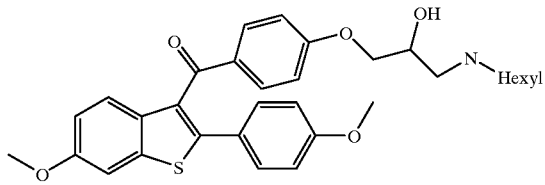

[6-Methoxy-2-(4-methoxyphenyl)benzo[b]thiophen-3-yl][O-epihydrin)-4-hydroxyphenyl]methanone (500 mg, 1.1 mmol) and n-hexylamine (0.74 mL, 5.6,mmol) were converted to 540 mg of the title compound by the procedure of Example 26.

Yield: 90%.

Example 38

[6-Hydroxy-2-(4-Hydroxyphenyl)benzo[b]thiophen-3-yl][4-(2-Hydroxy-3-Pentylaminopropoxy)phenyl] methanone

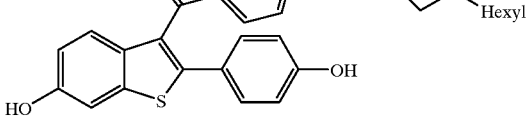

[6-Methoxy-2-(4-methoxyphenyl)benzo[b]thiophen-3-yl] [4-(2-methoxy-3-hexylaminopropoxy)phenyl]methanone (340 mg, 0.62 mmol) was converted to 200 mg of the title compound by the procedure of Example 32 using 0.23 mL (3.1 mmol) of ethanethiol 660 mg (5.0 mmol) of aluminum chloride.

Yield: 62%. $^1$H NMR (d$_6$-DMSO): d 7.61 (d, 2H, J=8.7 Hz), 7.30 (d, 1H, J=2.1 Hz), 7.20 (d, 1H, J=8.7 Hz), 7.13 (d, 2H, J=8.7 Hz), 6.84 (m, 3H), 6.63 (d, 1H, J=8.7 Hz), 3.89 (m, 3H), 2.50 (m, 2H), 1.19 (m, 8H), 0.80 (t, 3H, J=6.5 Hz).

Experimental Assays

Representative compounds of the present invention have been biologically tested to demonstrate their efficacy for treating the effects of post menopausal syndrome. In the examples illustrating the methods, a post menopausal model was used in which effects of different treatments upon circulating lipids were determined.

General Preparation Procedure

Seventy-five day old female Sprague Dawley rats (weight range of 200 g–225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, these rats were housed in metal hanging cases in groups of three or four animals per cage, and had ad libitum access to food (calcium content approximately 0.5%) and water for one week. Room temperature was maintained at 22.2° C.±1.7° C. with a minimum relative humidity of 40%. The photoperiod in the room was twelve hours light and twelve hours dark.

Dosing Regimen Tissue Collection.

After a one-week acclimation period (two weeks post-OVX), daily dosing with test compound was initiated. The test compounds or 17a-ethynylestradiol (Sigma Chemical Co., St. Louis, Mo.) were given orally, unless otherwise stated, as a suspension in 1% carboxymethylcellulose or dissolved in 20% cyclodextrin. Animals were dosed daily for four days. Following the dosing regimen, animals were weighed and anesthetized with a ketamine:xylazine (2:1, v:v) mixture and a blood sample was collected by cardiac puncture. The animals were then sacrificed by asphyxiation with CO$_2$, the uterus was removed through a midline incision, and a wet uterine weight was determined.

Serum Cholesterol Analysis

Blood samples were allowed to clot at room temperature for two hours, and serum was obtained following centrifugation for ten minutes at 3000 rpm. Serum cholesterol was determined using a high-performance cholesterol assay (Boehringer Mannheim Diagnostics, Indianapolis, Ind.). Briefly, the cholesterol was oxidized to produce cholest-4-en-3-one and hydrogen peroxide. The hydrogen peroxide was then reacted with phenol and 4-aminophenazone in the presence of peroxidase to produce a p-quinoneimine dye, which was read spectrophotometrically at 500 nm. Cholesterol concentration was then calculated against a standard curve.

Uterine Eosinophil Peroxidase (EPO) Assay

Uteri were kept at 4° C. until time of enzymatic analysis. The uteri were then homogenized in 50 volumes of 50 nM Tris buffer (pH=8.0) containing 0.005% Triton X-100. Upon addition of 0.01% hydrogen peroxide and 10 nM o-phenylenediamine (final concentrations) in Tris buffer, the increase in absorbance was monitored for one minute at 450 nm. The presence of eosonophils in the uterus was taken as an indication of estrogenic activity of a compound. The maximal velocity of a fifteen second interval was determined over the initial, linear portion of the reaction curve.

Representative compounds of the present invention were tested in a four day ovariectomized rat model to study their estrogenicity. In particular, the effect on the uterus and the cholesterol lowering characteristics were studied. Comparative data were obtained between untreated ovariectomized rats, ovariectomized rats treated with 17a-ethynylestradiol ($EE_2$), and ovariectomized rats treated with certain compounds of the present invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of untreated ovariectomized test animals. This uterine response to estrogen is well recognized in the art. Representative compounds of the present invention reduced serum cholesterol compared to the ovariectomized control animals. Also, relative to $EE_2$, representative compounds of the present invention have a diminished effect on uterine weight.

Compared to estrogenic compounds known in the art, the benefit of serum cholesterol reduction without as adverse of an affect on uterine weight is rare and desirable.

As is expressed in the in vivo data, estrogenicity also was assessed by evaluating the adverse response of eosinophil infiltration into the uterus. Relative to $EE_2$, which caused a substantial, expected increase in eosinophil infiltration, the representative compounds of the present invention did not increase the eosinophil infiltration, and in most cases had a significantly diminished effect.

In addition to the demonstrated benefits of these representative compounds of the present invention, especially when compared to estradiol, the compounds tested were not estrogen mimetic.

MCF-7 Proliferation Assay

The affinity of a representative sample of the compounds of the present invention for the estrogen receptors was tested in a MCF-7 receptor proliferation assay. MCF-7 breast adenocarcinoma cells (ATCC HTB 22) were maintained in MEM (minimal essential medium, phenol red-free, Sigma Chemical Co., St. Louis, Mo.) supplemented with 10% fetal bovine serum (FBS) (v/v), L-glutamine (2 mM), sodium pyruvate (1 mM), HEPES [N-(2-hydroxyethyl) piperazine-N'-2-ethanesulfonic acid 10 mM], non-essential amino acids and bovine insulin (1 mg/mL) (maintenance medium). Ten days prior to assay, MCF-7 cells were switched to maintenance medium supplemented with 10% dextran-coated charcoal stripped fetal bovine serum (DCC-FBS) assay medium) in place of 10% FBS to deplete internal stores of steroids. MCF-7 cells were removed from maintenance flasks using cell dissociation medium ($Ca^{+2}/Mg^{+2}$ free HBSS (phenol red-free) supplemented with 10 mM HEPES and 2 mM EDTA). Cells were washed twice with assay medium and adjusted to 80,000 cells/mL. Approximately 100 mL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 37° C. in a 5% $CO_2$ humidified incubator, microcultures were pulsed with tritiated thymidine (1 mCi/well) for four hours. Cultures were terminated by freezing at −70° C. for 4 hours followed by thawing and harvesting of microcultures using a Skatron Semiautomatic Cell Harvester. Samples were counted by liquid scintillation using a Wallac BetaPlace b-counter. Relative to 17b-estradiol's known effects on the proliferation of MCF-7, the representative compounds of the present invention demonstrated significantly less stimulatory activity. In most cases, no effect was observed at the highest concentrations tested, and in some cases an inhibitory effect was observed.

Administration and Formulation

For the majority of the methods of the present invention, compounds of formula I are administered continuously, from 1 to 3 times daily. However, cyclical therapy may especially be useful in the treatment of endometriosis or may be used acutely during painful attacks of the disease. In the case of restenosis, therapy may be limited to short (one to six months) intervals following medical procedures such as angioplasty.

The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 100 mg/day.

The compounds of this invention can be administered by a variety of routes including oral, rectal, transdermal, subcutaneous, intravenous, intramuscular, and intranasal, the selection of which will be decided by the attending physician. These compounds preferably are formulated prior to administration. Thus, another aspect of the present invention is a pharmaceutical composition comprising an effective amount of a compound of formula I, or a pharmaceutically acceptable salt thereof, optionally containing an effective amount of estrogen or progestin, and a pharmaceutically acceptable carrier, diluent, or excipient. The total active ingredients in such formulations comprises from 0.1% to 99.9% by weight of the formulation.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin;

resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyline glycols.

The compounds also can be formulated as elixirs or solutions for convenient oral administration or as solutions appropriate for parenteral administration, for example, by intramuscular, subcutaneous, or intravenous routes. Additionally, the compounds are well suited for formulation as sustained-release dosage forms and the like. The formulations can be so constituted that they release the active ingredient only or preferably in a particular physiological location, possibly over a period of time. The coatings, envelopes, and protective matrices may be made, for example, from polymeric substances or waxes.

The following formulation examples are illustrative only and are not intended to limit the scope of the present invention.

Formulations

In the formulations which follow, "active ingredient" means a compound of formula I, or a salt thereof.

Hard gelatin capsules are prepared using the following:

Formulation 1

Gelatin Capsules

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2

Tablets

| Ingredient | Quantity (mg/tablet) |
|---|---|
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5 mg–1000 mg of active ingredient are made up as follows:

Formulation 3

Tablets

| Ingredient | Quantity (mg/tablet) |
|---|---|
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C.–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1 mg–1000 mg of medicament per 5 ml dose are made as follows:

Formulation 4

Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5

Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6

| Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7

| Intravenous Solution | |
|---|---|
| Ingredient | Quantity |
| Active ingredient | 50 mg |
| Isotonic saline | 1,000 mL |

The solution of the above ingredients is intravenously administered to a patient at a rate of about 1 mL per minute.

Formulation 8

| Combination Capsule I | |
|---|---|
| Ingredient | Quantity (mg/capsule) |
| Active ingredient | 50 |
| Premarin | 1 |
| Avicel pH 101 | 50 |
| Starch 1500 | 117.50 |
| Silicon Oil | 2 |
| Tween 80 | 0.5 |
| Cab-O-Sil | 0.25 |

Formulation 9

| Combination Capsule II | |
|---|---|
| Ingredient | Quantity (mg/capsule) |
| Active ingredient | 50 |
| Norethynodrel | 5 |
| Avicel pH101 | 82.50 |
| Starch 1500 | 90 |
| Silicon Oil | 2 |
| Tween 80 | 0.50 |

Formulation 10

| Combination Tablet | |
|---|---|
| Ingredient | Quantity (mg/capsule) |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

The preferred embodiment of the present invention is now fully described. Nothing in this description is intended to limit the scope or spirit of this invention.

We claim:

1. A compound of formula I:

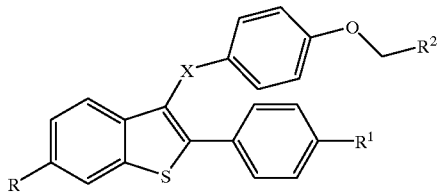

wherein:
R and $R^1$ are independently hydrogen, halo, hydroxy, or O—Pg;
$R^2$ is $CHR^3OR^4$, $CO_2R^5$, or a heterocycle;
  wherein said heterocycle is a 3 or 4 membered saturated, partially unsaturated, or aromatic optionally substituted ring, which contains one heteroatom chosen from oxygen or sulfur or is a 5 or 6 membered saturated, partially unsaturated, or aromatic optionally substituted ring, which contains one or two heteroatoms chosen from oxygen or sulfur;
X is C=O, CH=OH, $CH_2$, O, or S;
Pg is independently at each occurrence a hydroxy protecting group;
$R^3$ is hydrogen or $CH_2OH$;
$R^4$ is hydrogen, $C_1$–$C_6$ alkyl, or $COR^8$;
$R^5$ is hydrogen, $C_1$–$C_6$ alkyl, or aryl;
$R^8$ is hydrogen, $C_1$–$C_6$ alkyl, or aryl; with the proviso that when R and $R^1$ are both hydroxy or both O—Pg, Pg is methyl or methane sulfonyl, and X is C=O, then $R^3$ and $R^4$ are not both hydrogen, $R^5$ is not methyl, and said heterocycle is not a thienyl or tetrahydropyranyl moiety;
or a pharmaceutically acceptable salt or solvate thereof.

2. A compound according to claim 1 wherein X is C=O.

3. A compound according to claim 2 wherein $R^2$ is $CHR^3OR^4$, $R^3$ is hydrogen, and $R^4$ is hydrogen or $C_1$–$C_4$ alkyl.

4. A compound according to claim 3 wherein R and $R^1$ are independently O—Pg and Pg is independently at each occurrence $C_1$–$C_4$ alkyl or aryl.

5. A compound according to claim 4 wherein Pg is methyl, ethyl, t-butyl, phenyl, or benzyl.

6. A compound according to claim 2 wherein $R^2$ is $CHR^3OR^4$, $R^3$ is hydrogen, $R^4$ is $COR^8$, $R^8$ is hydrogen, $C_1$–$C_6$ alkyl, or aryl, and aryl is a phenyl or substituted phenyl group.

7. A compound according to claim 6 wherein R and $R^1$ are independently hydroxy or O—Pg and Pg is independently at each occurrence $C_1-C_4$ alkyl or aryl.

8. A compound according to claim 7 wherein Pg is methyl, ethyl, t-butyl, phenyl, or benzyl.

9. A compound according to claim 7 wherein R and $R^1$ are both hydroxy.

10. A compound according to claim 2 wherein $R^2$ is $CO^2R^5$ and $R^5$ is hydrogen or $C_1-C_4$ alkyl.

11. A compound according to claim 10 wherein R and $R^1$ are independently hydroxy or O—Pg and Pg is independently at each occurrence $C_1-C_4$ alkyl or aryl.

12. A compound according to claim 11 wherein Pg is methyl, ethyl, t-butyl, phenyl, or benzyl.

13. A compound according to claim 11 wherein R and $R^1$ are both hydroxy.

14. A compound according to claim 2 wherein $R^2$ is a heterocycle where that heterocycle is a 3, 4, 5, or 6 membered saturated, partially unsaturated, or aromatic optionally substituted ring, which contains 1 or 2 oxygen atoms.

15. A compound according to claim 14 wherein R and $R^1$ are independently hydroxy or O—Pg and Pg is independently at each occurrence $C_1-C_4$ alkyl or aryl.

16. A compound according to claim 15 wherein Pg is methyl, ethyl, t-butyl, phenyl, or benzyl.

17. A compound according to claim 15 wherein R and $R^1$ are both hydroxy.

18. A compound according to claim 2 which is selected from the group consisting of: [6-Methoxy-2-(4-Methoxyphenyl)benzo[b]thiophen-3-yl][(4-t-Butoxyethoxy)phenyl]methanone; [6-Methoxy-2-(4-Methoxyphenyl)benzo[b]thiophen-3-yl][(4-Hydroxyethoxy)phenyl]methanone; [6-Methoxy-2-(4-Methoxyphenyl)benzo[b]thiophen-3-yl][4-(Ethoxyethoxy)phenyl]methanone; [6-Hydroxy-2-(4-Hydroxyphenyl)benzo[b]thiophen-3-yl][4-(Ethoxyethoxy)phenyl]methanone; [6-Hydroxy-2-(4-Hydroxyphenyl)benzo[b]thiophen-3-yl][4-Carbomethoxymethoxyphenyl]methanone; [6-Hydroxy-2-(4-Hydroxyphenyl)benzo[b]thiophen-3-yl][4-Carboxymethoxyphenyl]methanone; [6-Methoxy-2-(4-Methoxyphenyl)benzo[b]thiophen-3-yl][4-(Tetrahydropyran-2-yl)methoxyphenyl]methanone; [6-Methoxy-2-(4-Methoxyphenyl)benzo[b]thiophen-3-yl][4-([Tetrahydrofuran-2-yl]methoxy)phenyl]methanone; [6-Hydroxy-2-(4-Hydroxyphenyl)benzo[b]thiophen-3-yl][4-([Tetrahydrofuran-2-yl]methoxy)phenyl]methanone; [6-Methoxy-2-(4-Methoxyphenyl)benzo[b]thiophen-3-yl][4-([2,2-Dimethyl-1,3-dioxolan-3-yl]methoxy)phenyl] methanone; [6-Hydroxy-2-(4-Hydroxyphenyl)benzo[b]thiophen-3-yl][4-(2,3-Dihydroxypropoxy)phenyl]methanone; (R)-[6-Methoxy-2-(4-Methoxyphenyl)benzo[b]thiophen-3-yl][4-([2,2-Dimethyl-1,3-dioxolan-3-yl]methoxy)phenyl]methanone; (R)-[6-Hydroxy-2-(4-Hydroxyphenyl)benzo[b]thiophen-3-yl][4-(2,3-Dihydroxypropoxy)phenyl]methanone; [6-Methoxy-2-(4-Methoxyphenyl)benzo[b]thiophen-3-yl][4-(Cyclohexanoyloxyethoxy)phenyl]methanone; [6-Hydroxy-2-(4-Hydroxyphenyl)benzo[b]thiophen-3-yl][4-(Cyclohexanoyloxyethoxy)phenyl]methanone; [6-Methoxy-2-(4-Methoxyphenyl)benzo[b]thiophen-3-yl][4-(Benzoyloxyethoxy)phenyl]methanone; [6-Hydroxy-2-(4-Hydroxyphenyl)benzo[b]thiophen-3-yl][4-(Benzoyloxyethoxy)phenyl]methanone; [6-Methoxy-2-(4-Methoxyphenyl)benzo[b]thiophen-3-yl][4-(Acetoxymethoxy)phenyl]methanone; [6-Hydroxy-2-(4-Hydroxyphenyl)benzo[b]thiophen-3-yl][4-(Acetoxymethoxy)phenyl]methanone; [6-Methoxy-2-(4-Methoxyphenyl)benzo[b]thiophen-3-yl][4-(Trimethylacetoxymethoxy)phenyl]methanone; [6-Hydroxy-2-(4-Hydroxyphenyl)benzo[b]thiophen-3-yl][4-(Trimethylacetoxymethoxy)phenyl]methanone; [6-Methoxy-2-(4-Methoxyphenyl)benzo[b]thiophen-3-yl][O-Epihydrin)-4-Hydroxyphenyl]methanone; or a pharmaceutically acceptable salt or solvate thereof.

19. A pharmaceutical formulation comprising a compound of claim 1 and a pharmaceutically acceptable carrier, diluent, or excipient.

20. A formulation according to claim 19 wherein said compound of formula I is a compound wherein X is C=O.

21. A method for treating the symptoms of postmenopausal syndrome which comprises administering to a woman in need of such treatment an effective amount of a compound of claim 1.

22. A method according to claim 21 wherein said formula I compound is a compound wherein X is C=O.

23. A method according to claim 21 wherein the postmenopausal syndrome pathological condition is osteoporosis.

24. A method according to claim 21 wherein the postmenopausal syndrome pathological condition is related to a cardiovascular disease.

25. A method according to claim 21 wherein said postmenopausal syndrome is estrogen related breast cancer.

* * * * *

UNITED STATES PATENT AND TRADEMARK OFFICE
CERTIFICATE OF CORRECTION

PATENT NO.   : 6,090,843
DATED        : July 18, 2000
INVENTOR(S)  : Henry Uhlman Bryant and Jeffrey Alan Dodge It is certified that error appears in the above-identified patent and that said Letters Patent is hereby corrected as shown below:

In column 36, line 43 should read "X is C=O CH-OH, $CH_2$, O, or S;"

Signed and Sealed this

First Day of May, 2001

Attest:

NICHOLAS P. GODICI

Attesting Officer    Acting Director of the United States Patent and Trademark Office